United States Patent
Schaus

(10) Patent No.: US 7,998,985 B2
(45) Date of Patent: Aug. 16, 2011

(54) 1,5-DIPHENYL-3-PYRIDINYLAMINO-1,5-DIHYDROPYRROLIDIN-2-ONE AS CB1 RECEPTOR MODULATOR

(75) Inventor: John Mehnert Schaus, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 247 days.

(21) Appl. No.: 12/444,692

(22) PCT Filed: Oct. 22, 2007

(86) PCT No.: PCT/US2007/082041
§ 371 (c)(1), (2), (4) Date: Apr. 8, 2009

(87) PCT Pub. No.: WO2008/070305
PCT Pub. Date: Jun. 12, 2008

(65) Prior Publication Data
US 2010/0016375 A1 Jan. 21, 2010

Related U.S. Application Data

(60) Provisional application No. 60/862,540, filed on Oct. 23, 2006.

(51) Int. Cl.
*A61K 31/4439* (2006.01)
*C07D 401/12* (2006.01)

(52) U.S. Cl. .................. 514/343; 546/278.4
(58) Field of Classification Search ............... 546/278.4; 514/343
See application file for complete search history.

(56) References Cited

FOREIGN PATENT DOCUMENTS

| | | | |
|---|---|---|---|
| WO | WO 2005/077911 A | 8/2005 | |
| WO | WO 2005/080345 A | 9/2005 | |
| WO | WO 2007/020502 A | 2/2007 | |

OTHER PUBLICATIONS

Piomelli, et al., "Review—The endocannabinoid system as a target for therapeutic drugs", *TIPS*—vol. 21-218-224 (2000).
Goya, et al., "Recent advances in cannabinoid receptor agonists and antagonists" *Exp. Opin. Ther. Patents* vol. 10 (10), 1529-1538 (2000).
Xiang, et al., "Pharamacology of Cannabinoid Receptor Agonists and Antagonists". *Annual Report in Medicinal Chemistry*—Academic Press, NY—vol. 34. 199-208.
Francis Barth, "Cannabinoid receptor agonists and antagonists", *Expert Opinion on Therapeutic Patents*—vol. 8(3) 301-313 (1998).
Andreichikov, et al. "Five membered 2,3-dioxo heterocycles, I. Synthesis and structure of 1,5-d", *Zhurnal Organicheskoi Khimii*—22(10) 2208-13 (1986).

*Primary Examiner* — Patricia Morris
(74) *Attorney, Agent, or Firm* — R. Craig Tucker

(57) ABSTRACT

Compound and pharmaceutical compositions comprising the compounds of the Formula

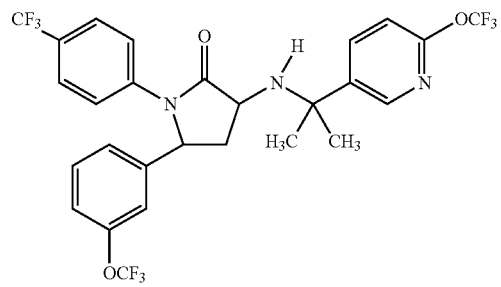

or a pharmaceutically acceptable salt thereof, as a $CB_1$ receptor inverse agonist, useful for reducing body weight in mammals, treating cognitive impairment associated with schizophrenia, and mitigating treatment emergent weight gain observed during treatment with antipsychotics.

5 Claims, No Drawings

1,5-DIPHENYL-3-PYRIDINYLAMINO-1,5-DIHYDROPYRROLIDIN-2-ONE AS CB1 RECEPTOR MODULATOR

This U.S. national stage application of International Application PCT/US2007/082041, filed Oct. 22, 2007, claims priority to U.S. provisional application Ser. No. 60/862,540, filed Oct. 23, 2006.

BACKGROUND OF THE INVENTION

The $CB_1$ receptor family is primarily found in the central and peripheral nervous systems and to a lesser extent in several peripheral organs. The $CB_2$ receptor is found primarily in the immune system. The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. 2000, 10, 1529-1538; Trends in Pharma. Sci. 2000, 21, 218-224). $CB_1$ receptor agonists have been associated with stimulation of feeding, anemetic properties, analgesia, reduction in intraocular pressure in glaucoma, and alleviation of muscle spasms in multiple sclerosis. Conversely, $CB_1$ receptor antagonists have been shown effective for reducing feeding and body weight in animal models of obesity. However, most compounds that modulate CB1 receptor activity have the pharmacological property of inverse agonism which reduces basal CB1 receptor signal transduction as well as the activity of blocking CB1 agonist dependent receptor stimulation.

A number of selective, centrally acting $CB_1$ receptor compounds are currently in development for the treatment of obesity. Nevertheless, there still remains a need for $CB_1$ receptor compounds which have increased in vivo potency which are low molecular weight, and have pharmacokinetic and pharmacodynamic properties that provide therapeutic benefit while minimizing adverse events. See for example WO 2007/020502.

In addition to appentency disorders, $CB_1$ inverse agonists have been shown to further potentiate the activity of antipsychotic agents in assays. Although current antipsychotic therapies are more or less effective at controlling positive symptoms, such therapies are not as effective in treating the negative and cognitive symptoms, rendering many patients incapable of leading normal lives. Convergent evidence suggests drugs that enhance neuronal activation in specific brain areas, hippocampal, striatal, and cortical areas in particular, would be effective in treating both negative and cognitive symptoms. In addition, the weight loss effects of $CB_1$ receptor compounds have been demonstrated in animal models of antipsychotic treatment-induced weight gain and therefore may also be effective in controlling the treatment-emergent weight gain and metabolic syndrome seen with current antipsychotic therapies.

Moreover, $CB_1$ receptor compounds have been shown to reduce alcohol consumption in animal models of alcohol drinking and therefore may be useful in the treatment of substance abuse.

While oral administration is a preferred route of drug delivery, many $CB_1$ receptor compounds suffer from poor oral bioavailability as a consequence of their limited solubility in aqueous media and their metabolic lability. Because of the high lipophilicity of the endogenous cannabinoid ligands and the complementary site to which they bind in the $CB_1$ receptor, known $CB_1$ receptor compounds are also highly lipophilic. This high lipophilicity leads to poor solubility in aqueous media which limits oral absorption and bioavailability. See for example WO 2007/020502.

In addition, compounds which are rapidly metabolized by the liver may undergo metabolic conversion following absorption from the small intestine and prior to reaching the general circulation. During this process, reactive metabolic intermediate (s) may be formed and subsequently may react with other nucleophiles in the body (such as proteins, DNA, RNA, etc.). This could lead to toxicity issues. This so-called "first pass effect" also limits drug bioavailability. See for example WO 2007/020502.

In conclusion, there is a need for $CB_1$ receptor compounds that have good bioavailability, have increased in vivo potency, are highly selective over $CB_2$, are more readily soluble than previous molecules, and do not form reactive metabolites which could subsequently cause toxicity issues. The present invention satisfies this need and provides related advantages as well.

SUMMARY OF THE INVENTION

The present invention provides a compound of Formula (I)

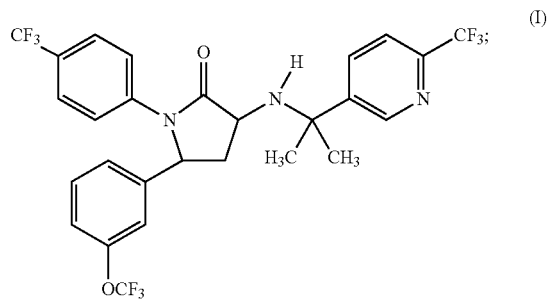

or a pharmaceutically acceptable salt thereof.

The present invention further provides a compound of Formula (Ia)

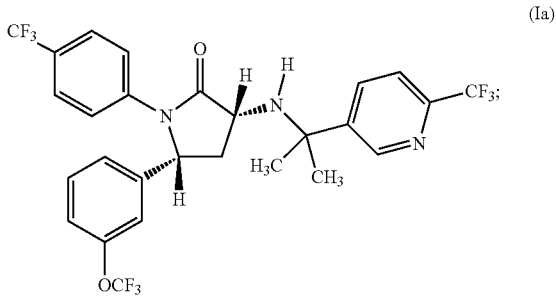

or a pharmaceutically acceptable salt thereof.

The present invention provides an intermediate of the compound of Formula (II)

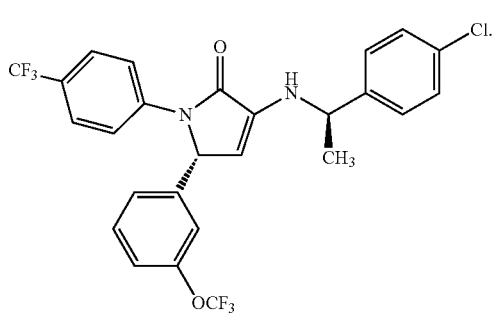

The present invention provides a pharmaceutical composition comprising a compound according to any of Formulas (I) or (Ia) and a pharmaceutically acceptable carrier, diluent, or excipient.

In another embodiment, the present invention provides the pharmaceutical composition, wherein the compound of Formula (Ia) is present in optical purity greater than 90% ee.

In yet another embodiment, the pharmaceutical composition, wherein the compound of Formula (Ia) is present in optical purity greater than 95% ee.

An embodiment of the present invention provide a compound according to any one of Formula (I) or (Ia) for use therapy.

The present invention provides a compound according to any one of Formula (I) or (Ia) for use in the treatment of a disorder selected from: an eating disorder associated with excessive food intake, obesity, schizophrenia, cognitive impairment associated with schizophrenia, substance abuse or alcohol dependence, smoking cessation and treatment emergent weight gain observed during treatment with an atypical antipsychotic.

The present invention provides the use of a compound according to any one of Formula (I) or (Ia) in the manufacture of a medicament for the treatment of a disorder selected from: an eating disorder associated with excessive food intake, obesity, schizophrenia, cognitive impairment associated with schizophrenia, substance abuse or alcohol dependence, smoking cessation and treatment emergent weight gain observed during treatment with an atypical antipsychotic.

An embodiment of the invention provides a method of treating a condition in a mammal which is treatable by blockade of $CB_1$ receptors via an inverse agonism mechanism, the method comprising administering to a patient an effective amount of a compound according to any one of Formula (I) or (Ia), or a pharmaceutically acceptable salt thereof.

An embodiment of the invention provides a method of treating a condition in a mammal an effective amount of a compound, according to any of Formulas (I) or (Ia), in simultaneous, separate, or sequential combination with an antipsychotic agent, or a pharmaceutically acceptable salt thereof.

An embodiment of the invention provides the method, wherein the condition is an eating disorder associated with excessive food intake.

An embodiment of the invention provides the method, wherein the condition is obesity.

An embodiment of the invention provides the method, wherein the condition is schizophrenia.

An embodiment of the invention provides the method, wherein the condition is cognitive impairment associated with schizophrenia.

An embodiment of the invention provides the method, wherein the condition is substance abuse or alcohol dependence.

An embodiment of the invention provides the method, wherein the condition is smoking cessation.

An embodiment of the invention provides the method, wherein the condition is treatment emergent weight gain observed during smoking cessation.

An embodiment of the invention provides a compound according to any one of Formula (I) or (Ia) for use in simultaneous, separate or sequential combination with an antipsychotic agent in the treatment of a disorder selected from: weight gain, obesity, schizophrenia, cognitive impairment associated with schizophrenia, substance abuse or alcohol dependence, smoking cessation and treatment emergent weight gain observed during treatment with an atypical antipsychotic.

In yet another embodiment, the invention provides the use of a compound according to any one of Formula (I) or (Ia) in the manufacture of a medicament for use in combination therapy for the treatment of a disorder selected from: weight gain, obesity, schizophrenia, cognitive impairment associated with schizophrenia, substance abuse or alcohol dependence, smoking cessation and treatment emergent weight gain observed during treatment with an atypical antipsychotic, wherein said medicament is to be administered in simultaneous, separate or sequential combination with an antipsychotic agent.

The present invention provides a method of treating a condition in a mammal which is treatable by blockade of $CB_1$ receptors via an inverse agonism mechanism in simultaneous, separate or sequential combination with an antipsychotic agent, the method comprising administering to a patient an effective amount of a compound according to any one of Formula (I) or (Ia), or a pharmaceutically acceptable salt thereof.

The present invention provides a method of treating a condition in a mammal comprising administering to the mammal an effective amount of a compound, according to any one of Formulas (I) or (Ia), or a pharmaceutically acceptable salt thereof.

An embodiment of the invention provides the method, wherein the condition is schizophrenia.

An embodiment of the invention provides the method, wherein the condition is weight gain.

An embodiment of the invention provides the method, wherein the condition is obesity.

An embodiment of the invention provides the method, wherein the condition is cognitive impairment associated with schizophrenia.

An embodiment of the invention provides the method, wherein the condition is substance abuse or alcohol dependence.

An embodiment of the invention provides the method, wherein the condition is smoking cessation.

An embodiment of the invention provides the method, wherein the condition is treatment emergent weight gain observed during treatment with an atypical antipsychotic.

Compounds of Formula (I) contain asymmetric centers and can thus occur as diastereomeric mixtures, racemic mixtures, single enantiomers, and individual diastereomers, such as compounds of Formula Ia. All such isomeric forms of the compounds of Formula (I) are contemplated as aspects of the present invention.

While compounds of Formula (I) in their racemic form are useful agents, it is generally preferable to administer compounds of Formula (I) in which one of the enantiomeric forms has been enriched. A preferred aspect of this invention provides compounds of Formula (Ia) that are substantially pure enantiomers. As such, each of the following specific classes of compounds of Formulas (I) and (Ia) are contemplated as aspects of the present invention:
  (a) Those where enantiomeric purities are greater than 80% enantiomeric excess;
  (b) Those where enantiomeric purities are greater than 90% enantiomeric excess;
  (c) Those where enantiomeric purities are greater than 95% enantiomeric excess; and
  (d) Those where enantiomeric purities are greater than 99% enantiomeric excess.

These enantiomerically pure compounds may be prepared by purification of the desired enantiomer of a compound of Formula (I) from a mixture of enantiomers of this compound. The desired enantiomer of a compound of Formula (I) may also be prepared by synthesis according to the following general schemes by using precursors that are substantially enantiomerically pure. Those skilled in the art will recognize that either resolution of final compounds or of intermediates will provide compounds of Formula (I) in substantially enantiomerically pure form, to yield for example, compounds of Formulas (Ia), and will employ the method which is most convenient.

It will be further recognized that a substantially pure diastereomer may be isolated from a mixture of diastereomers using methods known in the art. Methods for purification of diastereomers include chromatography and crystallization. A mixture of enantiomers may be separated into the individual substantially pure enantiomers by the process known as resolution. Enantiomers may be resolved through the use of chromatography using a chiral stationary phase. Suitable chiral solid phases include polysaccharide-based stationary phases such as Chiralpak AD and Chiracel OJ (sold by Chiral Technologies, Inc.). Additionally, enantiomers of basic compounds may be resolved by conversion to a mixture of diastereomeric salts by treatment with a chiral acid. The desired diastereomeric salt is isolated by, for example, crystallization. The substantially enantiomerically pure basic compound may be isolated by treatment with base. Examples of chiral acids include (−)-tartaric acid, (+)-tartaric acid, (−)-mandelic acid, (+)-mandelic acid, (−)-ditoluoyltartaric acid and (+)-ditoluoyltartaric acid. Enantiomers of acidic compounds may be resolved in an analogous manner using a substantially enantiomerically pure base. Examples of such bases include R-alpha-methylbenzylamine, S-alpha-methylbenzylamine, and brucine. Another method for the resolution of a racemic mixture involves reaction with a substantially enantiomerically pure chiral reagent (referred to here as a chiral auxiliary) to form a covalent bond. This reaction results in a mixture of diastereomers, which is purified according to methods known in the art. All, or a portion, of the chiral auxiliary may then be cleaved from the molecule to generate a compound which is substantially enantiomerically pure. In some cases, the asymmetric center introduced by the chiral auxiliary may be retained in the final product.

One of ordinary skill in the art will recognize that certain disclosed intermediate compounds and the compound of Formula (II) may exist with different points of attachment of hydrogen, and is thus considered tautomeric. The individual tautomers as well as mixtures thereof are contemplated as an aspect of the present invention. Each of the forms of the tautomer may exist, interconvert, and undergo the tautomerization under the conditions specified.

It will be understood that as used herein, unless otherwise specified, references to the compounds of Formulas (I) or (Ia) are meant to also include the pharmaceutically acceptable salts thereof.

It will be understood that the compounds of the present invention described below may exist as distinct crystal forms prepared by crystallization under controlled conditions.

Compounds of Formulas (I) and (Ia) are selective for the $CB_1$ receptor in preference to the $CB_2$ receptor. In addition, there is evidence suggesting these $CB_1$ receptor ligands act as antagonists of $CB_1$ receptor function and have inverse agonists properties as well. Thus, it can be stated compounds of Formulas (I) and (Ia) are modulators of the $CB_1$ receptor, and as such are useful for prevention and treatment of conditions associated with the $CB_1$ receptor. Such conditions include, for example, memory deficits, cognitive disorders, negative symptoms of schizophrenia, substance abuse disorders (particularly to opiates, alcohol, and nicotine), obesity, metabolic disorders and eating disorders associated with excessive food intake. See DSM-IV-TR., *Diagnostic and Statistical Manual of Mental Disorders. Revised,* $4^{th}$ Ed., Text Revision (2000). See also DSM-IV, *Diagnostic and Statistical Manual of Mental Disorders* $4^{th}$ Ed., (1994). The DSM-UV and DSM-IV-TR were prepared by the Task Force on Nomenclature and Statistics of the American Psychiatric Association, and provides descriptions of diagnostic categories. The skilled artisan will recognize that there are alternative nomenclatures, nosologies, and classification systems for pathologic psychological conditions and that these systems evolve with medical scientific progress.

The compounds of Formulas (I) or (Ia) can also be used to ameliorate weight gain, whether or not the associated weight gain subject can be classified as clinically obese.

An effective amount of the compounds of Formulas (I) or (Ia), may be administered to a patient in need of such treatment or prophylaxis in order to practice the present methods of therapy. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment. The prophylactic or therapeutic dosage of a compound of Formula (I) or (Ia) will, of course, vary with the nature of the severity of the condition to be treated and with the particular compound of Formula (I) or (Ia) and its route of administration.

The dose may be administered in a single daily dose or the total daily dosage may be administered in divided doses of two, three or four times daily. Furthermore, based on the properties of the individual compound selected for administration and/or the characteristics of the dosage form (i.e., modified release), the dose may be administered less frequently, e.g., weekly, twice weekly, monthly, etc. The unit dosage may be correspondingly larger for the less frequent administration. When administered via, transdermal routes, or through a continual intravenous solution, the dosage administration will, of course, be continuous rather than intermittent throughout the dosage regimen.

DETAILED DESCRIPTION

As used above and throughout the description of the invention, the following terms, unless otherwise indicated, shall be defined as follows:

"Agonist" and "agonists" shall refer to those compounds which stimulate the functional response of a receptor.

"Neutral antagonist" and "neutral antagonists" shall refer to those compounds which do not alter the basal activity of a receptor but block the functional activity of agonists and inverse agonists by returning the functional response to that of the basal state.

"Inverse agonist" and "inverse agonists" shall refer to those compounds which possess negative intrinsic activity by reversing the constitutive activity of the receptor. Inverse agonists act as antagonists to reverse the activity of agonists.

"Antagonist" or "antagonists" shall refer to those compounds which are neutral antagonists.

"Obesity" refers to the condition of having a high amount of body fat. A person is considered obese if he or she has a body mass index (BMI) of 30 kg/m$^2$ or greater. A person with BMI=27-30 is generally considered overweight. Conventionally, those persons with normal weight have a BMI of 19.9 to 25.9. The obesity may be due to any cause, whether genetic or environmental. Examples of disorders that may result in obesity or be the cause of obesity include overeating, decreased physical activity and pathological conditions showing reduced metabolic activity.

"Pharmaceutically acceptable salts" and "salts" refer to the relatively non-toxic, inorganic and organic acid addition salts, and base addition salts, of compounds of the present invention. See, for example S. M. Berge, et al., "Pharmaceutical Salts," *J. Pharm. Sci.*, 66, 1-19 (1977).

"Pharmaceutical composition" and "composition" are intended to encompass a product comprising the active ingredient, preferably present in pharmaceutically effective amounts, and the inert ingredient(s) (pharmaceutically acceptable excipients) that make up the carrier, as well as any product which results, directly or indirectly from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I) or (Ia) and any pharmaceutically acceptable excipients.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity (e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis).

"Treating," as used herein, unless otherwise indicated, means reversing, alleviating, inhibiting the progress of, or preventing the disorder or condition to which such term applies, or one or more symptoms of such disorder or condition. The term "treatment" as used herein, unless otherwise indicated, refers to the act of treating as "treating" is defined immediately above.

"p.o.," as used herein, unless otherwise indicated, means orally.

"s.c." as used herein, unless otherwise indicated mean subcutaneous.

"Ret.," as used herein, unless otherwise indicated, mean retention.

"DMSO," as used herein, unless otherwise indicated, means dimethyl sulfoxide.

For the therapeutic utility taught herein, the salt of the claimed compounds must be pharmaceutically acceptable. For further details on pharmaceutically acceptable salts, see Journal of Pharmaceutical Science, 66, 1 (1977).

PREPARATIONS AND EXAMPLES

Conditions for HPLC Methods referred to throughout the Preparations and Examples:

Method A

LC column: Zorbax Eclipse XDB C8 4.6×150 mm 5 uM; Gradient: 20-90% acetonitrile w/0.01% trifluoracetic acid in 13.0 minutes. Column temperature: 40° C.; autosampler temperature: ambient; Flow rate: 2.0 mL/minute; Signal detected at 260 and 215 nM wavelengths.

Method B

LC column: Zorbax SB-phenyl 4.6×150 mm 5 μm

Isocratic: 36% A and 64% B, where A=0.05 M NH$_4$OAc in water (pH 5.0) and B=ACN for 10 minutes. Column temperature: 35° C.

Autosampler temperature: ambient

Flow rate: 2.0 mL/minute

Signal detected at 206 nM wavelength.

Method C

LC column: Zorbax RX-C18 4.6×250 mm 5 μm

Gradient: 50-90% acetonitrile w/0.03 M Phosphate Buffer (Phosphate Buffer=5.52 g NaH$_2$PO$_4$ and 1.4 mL H$_3$PO$_4$ in 2 L Milli-Q H$_2$O) in 15 minutes. Column temperature: 40° C.

Autosampler temperature: ambient

Flow rate: 1.5 mL/minute

Signal detected at 260 nM wavelength.

Method D

LC Column: Phenomenex Gemini C$_{18}$ 2.0×50 mm 3.0 μM

Gradient: 5-100% ACN ACN w/0.1% Formic Acid in 7.0 min. then held at 100% for 1.0 min.

Column Temp: 50° C.+/− 10° C.

AS Temp: Ambient

Flow Rate: 1.0 mL/min.

Signal detected at 300 nM wavelength.

MS (m/z): 402 (M−1).

Preparation A

6-Trifluoromethyl-nicotinic acid ethyl ester

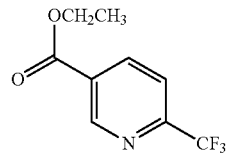

Prepare the titled compound, via the procedure described in the German patent entitled "Preparation of 6-(haloalkyl)-3-pyridinecarboxylic acids". Mueller, Peter. (Bayer A.-G., Germany). Eur. Pat. Appl. (2003), 13 pp. EP 1340747 A1

20030903. ¹H NMR (DMSO-d₆, 500 MHz): δ 9.19 (s, 1H), 8.53 (dd, 1H, J=1.5, 8.5), 8.04 (d, 1H, J=8), 4.38 (q, 2H, J=7), 1.34 (t, 3H, J=7).

Preparation B 2-(6-Trifluoromethyl-pyridin-3-yl)-propan-2-ol

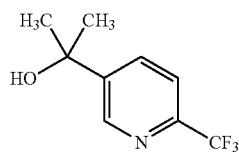

Cool the contents of an inerted reaction vessel containing technical grade 6-trifluoromethyl-nicotinic acid ethyl ester (45.6 moles; 10.00 kg) and tert-butyl methyl ether (71.6 L; 53.0 kg) to 10-15° C., and add the solution into a separate inerted reaction vessel cooled to 5-12° C. containing 3 M methylmagnesium chloride (136.8 moles; 45.6 L; 46.2 kg) and tetrahydrofuran (76.5 L; 68.0 kg). Observe a moderate exotherm during the addition, and maintain the internal reaction temperature between 15-25° C. Confirm that the starting ester is completely consumed by HPLC, and cool the reactor contents to 0-3° C. Add the contents from the reaction vessel slowly to a separate reactor cooled to 0-5° C. containing hydrochloric acid (203 moles; 16.67 L; 20.0 kg) and water (81.0 L, 81.0 kg), and observe gas evolution. Separate the layers and extract the aqueous phase once with tert-butyl methyl ether (59.5 L; 44.0 kg). Combine the organic layers and wash with a 20% sodium chloride solution (189.3 moles; 46.5 L; 55.3 kg). Filter the organic solution, concentrate to approximately 1 volume, and dilute with acetonitrile (31.8 L; 25.0 kg). Concentrate the solution to approximately 1 volume to provide the titled compound as a technical grade oil (7.9 kg; 84.4%, based on HPLC) in acetonitrile. Use the crude material as a solution in acetonitrile without further purification. A pure sample of the product can be obtained by following the procedure given below.

Purification (Optional): Charge the titled compound (1.81 kg, 8.82 moles) to a 22-L separatory funnel with methyl t-butyl ether (3 L, 2.2 Kg), water (500 mL) and saturated aqueous sodium bicarbonate (500 mL) and stir for 10 minutes Separate the bright yellow aqueous layer and transfer the organic phase to a 22-L flask. Add magnesium sulfate (200 g, 1.66 moles) to the flask, stir 10 minutes then filter. Concentrate the filtrate to an oil and co-evaporate twice with acetonitrile (2×3 L) to afford the titled compound as an oil weighing 1.64 kg (90.6%). ¹H NMR (DMSO-d₆, 500 MHz): δ 8.85 (d, 1H, J=2.5 Hz), 8.10 (dd, 1H, J=2, 8 Hz), 7.81 (d, 1H, J=8 Hz), 5.42 (s, 1H), 1.47 (s, 6H).

Preparation C

N-[1-Methyl-1-(6-trifluoromethyl-pyridin-3-yl)-ethyl]-acetamide

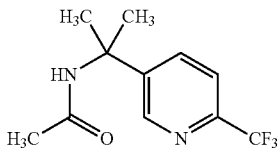

Add acetonitrile (67.4 L; 53.0 kg) to a reaction vessel containing 2-(6-trifluoromethyl-pyridin-3-yl)-propan-2-ol (52 moles; 12.8 kg) and cool to 0-5° C. Add concentrated sulfuric acid (372 moles; 19.8 L; 36.5 kg) slowly, maintaining the internal reaction temperature between 0-15° C. Heat the solution to 25-30° C. for 24 hours, and observe the completion of the reaction by HPLC. Cool the mixture to 0° C. while stirring and add water (95.0 L; 95.0 kg). Add a solution of aqueous ammonia (57.5 kg) to adjust the solution pH to 8.0-9.0, and then add tert-butyl methyl ether (81.1 L; 60.0 kg). Separate the lower aqueous layer, concentrate the organic layer to approximately 3 volumes, and cool the contents of the reaction to −5-0° C. Filter the resultant solids and dry under vacuum until constant weight and collect (13.4 kg; 87.3%, based on HPLC) of the titled compound as a pale yellow solid in 81.8% purity. ¹H NMR (DMSO-d₆, 500 MHz): δ 8.68 (d, 1H, J=2 Hz), 8.30 (s, 1H), 7.92 (dd, 1H, J=2.5, 8.5 Hz), 7.79 (d, 1H, J=5.8 Hz), 1.82 (s, 3H), 1.56 (s, 6H).

Preparation D

1-Methyl-1-(6-trifluoromethyl-pyridin-3-yl)-ethylamine

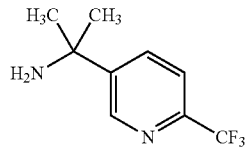

Heat a mixture of N-[1-Methyl-1-(6-trifluoromethyl-pyridin-3-yl)-ethyl]-acetamide (93.5 moles, 19.1 kg), concentrated hydrochloric acid (805.9 moles; 66.2 L; 79.4 kg), and water (79.4 L; 79.4 kg) to 95-100° C. with stirring under nitrogen for 24 hours. Cool the reaction mixture to 20-35° C. and observe completion of the reaction by HPLC. Cool the reaction vessel to 10-20° C. and add tert-butyl methyl ether (105.4 L; 78.0 kg). Separate the phases, and discard the organic layer. Add 15% sodium hydroxide (910.9 moles; 205 L; 242.9 kg) to the aqueous phase and observe a pH of 9.5-10.5. Extract the aqueous layer with ethyl acetate (3×89 mL; 3×80.0 kg), combine the organic layers, and discard the aqueous phase. Concentrate the solution to approximately 2 volumes, add tert-butyl methyl ether (174 L; 129.1 kg), and concentrate the solution to approximately 2 volumes. Dilute the reaction vessel with n-heptane (168 L; 115.0 kg), concentrate the solution to approximately 2 volumes, and dilute with additional n-heptane (30 L, 20.7 kg). Cool the contents of the reaction mixture to 0-5° C. and stir the mixture for 2 hours at 0-5° C. Filter and dry the resultant solids under vacuum at 35-45° C. to afford the titled compound (14.19 kg; 74.3%, based on HPLC) as a 97.9% pure tan powder.

Preparation E

1-Methyl-1-(6-trifluoromethyl-pyridin-3-yl)-ethylamine: compound with toluene-4-sulfonic acid

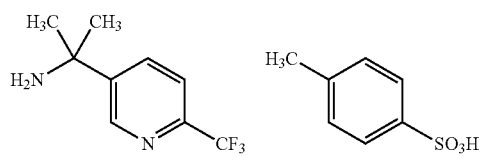

Add a solution of 1-Methyl-1-(6-trifluoromethyl-pyridin-3-yl)-ethylamine (280 g, 1.37 moles) in methyl t-butyl ether (1.4 L) to a solution of p-toluenesulfonic acid monohydrate (212.5 g, 1.23 moles) in tetrahydrofuran (980 mL). Observe a pH of 2.0 and an exotherm to 28° C. Cool to 18° C. and filter solids. Rinse filter cake with methyl t-butyl ether (1.4 L). Vacuum dry the filter cake at ambient temperature and collect 408 g (79%) of the titled compound as a white solid. $^1$H NMR (DMSO-$d_6$, 500 MHz): δ 8.94 (d, 1H, J=2.5), 8.53 (br s, 3H), 8.2 (dd, 1H, J=5.5, 8), 8.02 (d, 1H, J=8), 7.46 (d, 2H, J=8), 7.10 (d, 2H, J=7.5), 2.27 (s, 3H), 1.68 (s, 6H).

Preparation F

1-Methyl-1-(6-trifluoromethyl-pyridin-3-yl)-ethylamine

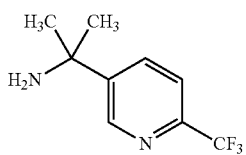

Weigh into 5-L 3-neck flask 1-methyl-1-(6-trifluoromethyl-pyridin-3-yl)-ethylamine; compound with toluene-4-sulfonic acid (990 g, 2.63 moles). Add methyl t-butyl ether (2.48 L) to form a suspension that is cooled by an ice-bath. Add a 5 M solution of sodium hydroxide (578.64 mL, 2.89 moles) to afford a biphasic mixture at pH 12.2. Separate the phases and extract the organic phase with water (125 mL). Remove the organic phase and concentrate under reduced pressure to afford a residue (200 g). Extract the aqueous phase with a mixture of methyl t-butyl ether (990 mL) and tetrahydrofuran (1.32 L). Separate the organic phase and concentrate under reduced pressure to afford another residue (200 g). Observe that the aqueous phase is pH 10.1 and add 5N NaOH (157.8 mL, 0.789 mol) to give pH 13. Extract the aqueous phase with dichloromethane (1.32 L). Separate the phases and concentrate the organic phase to a third residue. Combine the three residues of amine, suspend in heptane (1 L) with mixing, and concentrate the suspension to afford 427 g (79.5%) of the purified titled compound as a white crystalline solid. $^1$H NMR (CDCl$_3$, 500 MHz): δ 8.91 (d, 1H, J=2.5), 8.05 (dd, 1H, J=2, 8), 7.64 (d, 1H, J=8.5), 1.68 (br s, 2H), 1.55 (s, 6H).

Preparation G

1-Methyl-1-(6-trifluoromethyl-pyridin-3-yl)-ethylamine hydrochloride

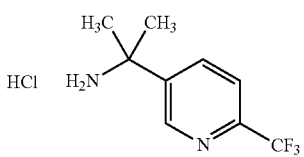

Dissolve 1-methyl-1-(6-trifluoromethyl-pyridin-3-yl)-ethylamine from Preparation F (1.0 g, 4.9 mmol) in acetone (10 mL) at ambient temperature and stir for 5 minutes. Add concentrated (12.18 N) hydrochloric acid (0.4 mL, 4.9 mmol) drop-wise with continued stirring, and observe the formation of a white solid. Cool the reaction mixture to 0° C. and continue stirring for 30 minutes. Filter the resultant solid and rinse with cold acetone (2 mL). Dry under vacuum at 40° C. to provide the titled compound (0.73 g, 62%) as a white solid: $^1$H NMR (400 MHz, DMSO-$d_6$) δ 9.17 (s (br), 3H), 9.02 (d, 1H, J=2.4 Hz), 8.32 (dd, 1H, J=8.0, 2.0 Hz), 7.97 (d, 1H, J=8.4 Hz), 1.71 (s, 6H); $^{13}$C NMR (100 MHz, DMSO-$d_6$) δ 148.0, 146.2 (q, $J_{CF}$=34.0 Hz), 142.4 (d, $J_{CF}$=0.8 Hz), 136.0, 121.9 (q, $J_{CF}$=273 Hz), 120.8 (t, $J_{CF}$=2.6 Hz), 54.9, 27.5.

Preparation H

(±)-5-(3-Trifluoromethoxy-phenyl)-1-(4-trifluoromethyl-phenyl)-3-(4-trifluoromethyl-phenylamino)-1,5-dihydro-pyrrol-2-one

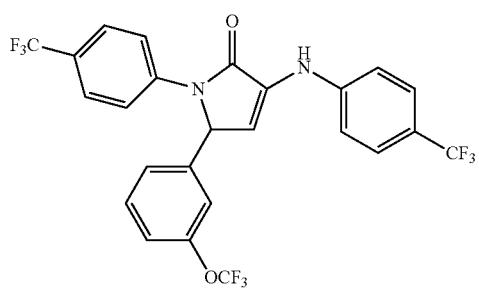

Stir 3-(trifluoromethoxy)-benzaldehyde (25.0 g, 132 mmol) and ethyl pyruvate (15.3 g, 132 mmol) in glacial acetic acid (125 mL) at ambient temperature for 10 minutes. Add 4-(trifluoromethyl)aniline (46.7 g, 290 mmol) drop-wise over 15 minutes with continued stirring, warm the solution to 30° C., and stir 22-24 h. Cool the solution to 26° C., add iso-propyl alcohol (125 mL) and water (125 mL). Stir the solution at room temperature for 15 minutes, filter the precipitate and wash with a 1:1 mixture of iso-propyl alcohol-water (100 mL×2). Dry under vacuum at 40° C. to afford the titled compound (60.46 g, 84%) as a white powder: HPLC (Method C) retention time: 10.9 minutes. MS (m/z): 545.1 (M−1). $^1$H NMR (500 MHz, DMSO-$d_6$) δ 8.76 (s, 1H), 7.86 (d, 2H, J=8.5 Hz), 7.70 (d, 2H, J=8.5 Hz), 7.56 (d, 2H, J=9.0 Hz), 7.47 (d, 2H, J=8.5 Hz), 7.44-7.41 (m, 1H), 7.37 (s, 1H), 7.29 (d, 1H, J=8.0 Hz), 7.22 (d, 1H, J=8.0 Hz), 6.66 (d, 1H, J=3.0 Hz), 6.29 (d, 1H, J=2.5 Hz).

Preparation I (R)-1-(4-Trifluoromethylphenyl)-3-[(1R)-1-(4-chlorophenyl)-ethylamino]-5-(3-trifluoromethoxyphenyl)-1,5-dihydropyrrol-2-one

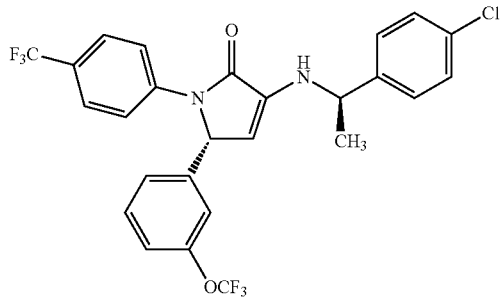

Mix ethanol (120 mL), glacial acetic acid (15 mL), water (3.0 mL, 164.7 mmol), trifluoroacetic acid (6.2 mL, 82.4 mmol), (±)-5-(3-trifluoromethoxy-phenyl)-1-(4-trifluoromethyl-phenyl)-3-(4-trifluoromethyl-phenylamino)-1,5-dihydro-pyrrol-2-one (30.0 g, 54.9 mmol), and 2,5-dimethoxytetrahydrofuran (10.7 mL, 82.4 mmol). Warm the solution to 50° C. and stir the reaction mixture for 15-18 hours. Discontinue heating the solution, add water (35 mL), and cool the reaction mixture to –19° C. Filter the slurry and wash the solid with a 1:4 mixture of water-methanol (20 mL). Transfer the filtrate to a separatory funnel and wash with 6% brine (280 mL), add 6% brine (100 mL), methanol (40 mL), diethyl ether (100 mL), and saturated sodium bicarbonate solution (43 mL) to the organic phase. Separate the layers, add methanol (60 mL) to the organic phase, and concentrate the solution to approximately 1 volume containing (±)-5-(3-trifluoromethoxy-phenyl)-1-(4-trifluoromethyl-phenyl)-pyrrolidine-2,3-dione. Add methanol (60 mL) and (R)-4-chloro-alpha-methylbenzylamine (7.8 mL, 55.0 mmol) and stir at room temperature for 24 hours. Monitor the reaction by HPLC for completion (Method B), then cool the solution to –7° C. and continue stirring at this temperature for 72 hours. Add a pre-mixed solution of potassium hydroxide (0.69 g, 10.5 mmol) in methanol (11 mL) to the reaction mixture, warm the solution to 10° C., and stir for an additional 4 hours. Cool the solution to –7° C., filter the slurry, and rinse the resultant product with methanol (5 mL×3). Dry the solid under vacuum to obtain (R)-1-(4-trifluoromethyl-phenyl)-3-[1(R)-(4-chloro-phenyl)-ethylamino]-5-(3-trifluoromethoxy-phenyl)-1,5-dihydro-pyrrol-2-one (12.3 g, 47.7%) as a white solid: HPLC (Method B) retention time: 4.3 minutes. MS (m/z): 539.0 (M−1). $^1$H NMR (500 MHz, DMSO-d$_6$) δ 7.76 (d, 2H, J=8.5 Hz), 7.62 (d, 2H, J=9.0 Hz), 7.38-7.36 (m, 2H), 7.30-7.27 (m, 3H), 7.10 (dd, 1H, J=8.5, 1.0 Hz), 7.05 (d, 1H, J=7.5 Hz), 6.95 (s, 1H), 6.06 (d, 1H, J=8.0 Hz), 5.96 (d, 1H, J=3.0 Hz), 5.22 (d, 1H, J=3.0 Hz), 4.35-4.32 (m, 1H), 1.43 (d, 3H, J=6.5 Hz).

Example 1

(3R,5R)-3-[1-Methyl-1-(6-trifluoromethyl-pyridin-3-yl)-ethylamino]-1-(4-trifluoromethyl-phenyl)-5-(3-trifluoromethoxy-phenyl)-pyrrolidin-2-one, 4-methylbenzenesulfonate (1:1)

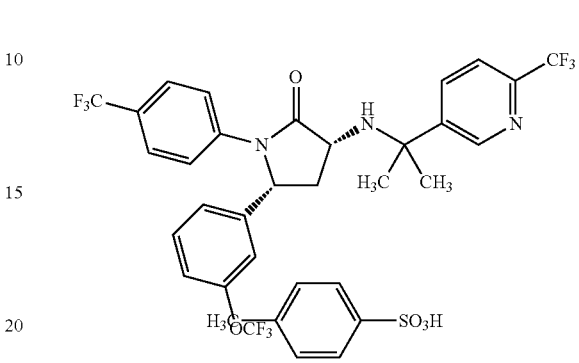

Stir (R)-1-(4-trifluoromethyl-phenyl)-3-[(1R)-1-(4-chlorophenyl)-ethylamino]-5-(3-trifluoromethoxyphenyl)-1,5-dihydropyrrol-2-one (50.0 g, 92.4 mmol), toluene (200 mL), and water (100 mL) at ambient temperature for 10 minutes. Add trifluoroacetic acid (50.0 mL, 0.66 mol) to the above biphasic solution and observe a slight exotherm (23 to 30° C.). Monitor the reaction by HPLC (method A), and after 1-2 hours transfer the solution to a separatory funnel and remove the aqueous layer. Wash the organic phase with 5 N hydrochloric acid (200 mL×2), water (200 mL), and assay the organic layer to ensure the removal of (R)-4-chloro-alpha-methylbenzylamine. Place the organic solution into a reaction flask and set aside. In a separate flask mix 1-methyl-1-(6-trifluoromethyl-pyridin-3-yl)-ethylamine hydrochloride (33.4 g, 138.6 mmol), toluene (150 mL), 2 N sodium hydroxide (110 mL, 212.6 mmol) and stir at ambient temperature for 30 minutes. Separate the organic layer and transfer to a clean flask. Stir the solution and add acetic acid (52 mL) to observe a slight exotherm (23 to 32° C.). Add the previous solution containing (5R)-5-(3-trifluoromethoxy-phenyl)-1-(4-trifluoromethyl-phenyl)-pyrrolidine-2,3-dione (37.3 g, 92.4 mmol theoretical) in toluene (200 mL) to the reaction mixture and heat to 45° C. with stirring for 14-18 hours. Check the solution by HPLC (Method A) to observe the disappearance of (5R)-3-hydroxy-5-(3-trifluoromethoxy-phenyl)-1-(4-trifluoromethyl-phenyl)-1,5-dihydro-pyrrol-2-one dimer (see below), and cool the solution to ambient temperature.

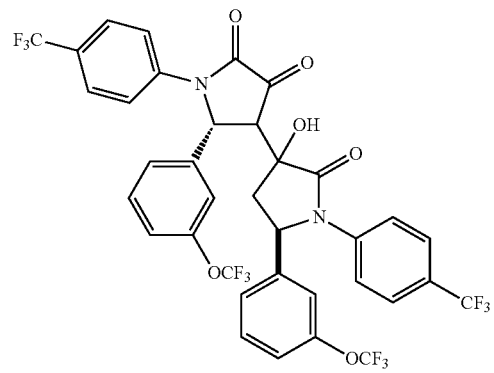

Transfer the solution to a separatory funnel and wash the purple solution with 3% aqueous sodium chloride (120 mL×2), saturated sodium bicarbonate solution (120 mL), and 3% brine (120 mL). Transfer the organic phase to a flask, concentrate to approximately 2 volumes (100 mL), and add fresh toluene (150 mL). Stir the purple reaction for 5 minutes under a nitrogen purge and add sodium triacetoxyborohydride (39.2 g, 184.9 mmol) in one portion at ambient temperature. Add trifluoroacetic acid (50.0 mL, 655.3 mmol) slowly to observe an exotherm (23 to 34° C.), being careful not to exceed an internal temperature of greater than 35° C. Stir the reaction at ambient temperature for 2-4 hours, and monitor the reaction by HPLC (method A) for completion. Add water (250 mL), methyl tert-butyl ether (150 mL) and separate the layers. Wash the organic layer with 2 N sodium hydroxide (150 mL), water, (150 mL×2), and transfer the organic phase containing the product to a flask. Concentrate the solution to approximately 2 volumes (100 mL), add fresh toluene (450 mL), and concentrate again to approximately 2 volumes (100 mL). Add fresh toluene (450 mL), warm the solution to 50° C. with stirring, and add p-toluenesulfonic acid monohydrate (14.1 g, 73.9 mmol) as a solution in ethanol (60 mL). Cool the reaction mixture to ambient temperature and stir for 1 hour. Filter the precipitate, wash with toluene (50 mL×2), and dry under vacuum at 40° C. to provide the titled compound (31.6 g, 44.8%) as a white powder: HPLC (Method A) retention time: 8.0 minutes. HRMS (m/z): 592.1641 (M+1). $^1$H NMR (500 MHz, DMSO-d$_6$) δ 9.08 (d, J=2.2 Hz, 1H), 8.42 (dd, J=8.2, 2.2 Hz, 1H), 8.02 (d, J=8.2 Hz, 1H), 7.64-7.62 (m, 2H), 7.52-7.47 (m, 4H), 7.41-7.38 (m, 1H), 7.33 (d, J=7.7 Hz, 1H), 7.28 (s, 1H), 7.19 (d, J=8.2 Hz, 1H), 7.11-7.10 (m, 2H), 5.37 (dd, J=9.3, 6.0 Hz, 1H), 4.34 (s, 1H), 2.78-2.72 (m, 1H), 2.27 (s, 3H), 2.04 (dd, J=21.4, 11.0 Hz, 1H), 1.88 (s, 3H), 1.87 (s, 3H).

Example 2

Purification of (3R,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one, 4-methylbenzenesulfonate (1:1)

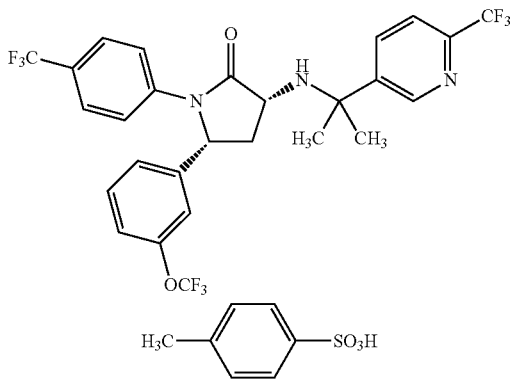

Mix (3R,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one, 4-methylbenzenesulfonate (1:1) (5.0 g, 6.55 mmol), toluene (75 mL), and 10% aqueous sodium carbonate solution (25 mL) at ambient temperature for 1 hour. Separate the layers and wash the organic phase with water (25 mL×2). Place the organic phase in a flask and concentrate to approximately 2 volumes (10 mL). Add fresh toluene (50 mL), concentrate the solution to approximately 2 volumes (10 mL), and add fresh toluene (65 mL). Warm the solution to 55° C. with stirring and add p-toluenesulfonic acid monohydrate (1.27 g, 6.55 mmol) as a solution in ethanol (5.5 mL). Cool the reaction mixture to ambient temperature and stir for 1 hour. Filter the resultant slurry, wash the solid with toluene (5 mL×2), and dry under vacuum at 40° C. to afford the titled compound (4.5 g, 90.4%) as a white crystalline solid: HPLC (Method A) retention time: 8.0 minutes. HRMS (m/z): 592.1641 (M+1). $^1$H NMR (500 MHz, DMSO-d$_6$) δ 9.08 (d, J=2.2 Hz, 1H), 8.42 (dd, J=8.2, 2.2 Hz, 1H), 8.02 (d, J=8.2 Hz, 1H), 7.64-7.62 (m, 2H), 7.52-7.47 (m, 4H), 7.41-7.38 (m, 1H), 7.33 (d, J=7.7 Hz, 1H), 7.28 (s, 1H), 7.19 (d, J=8.2 Hz, 1H), 7.11-7.10 (m, 2H), 5.37 (dd, J=9.3, 6.0 Hz, 1H), 4.34 (s, 1H), 2.78-2.72 (m, 1H), 2.27 (s, 3H), 2.04 (dd, J=21.4, 11.0 Hz, 1H), 1.88 (s, 3H), 1.87 (s, 3H).

(3R,5R)-3-[1-Methyl-1-(6-trifluoromethyl-pyridin-3-yl)-ethylamino]-1-(4-trifluoromethyl-phenyl)-5-(3-trifluoromethoxy-phenyl)-pyrrolidin-2-one, 4-methylbenzenesulfonate (1:1) can also be synthesized by utilizing:

Preparation Ia (S)-1-(4-Trifluoromethyl-phenyl)-3-((R)-1-phenyl-ethylamino)-5-(3-trifluoromethoxy-phenyl)-1,5-dihydro-pyrrol-2-one

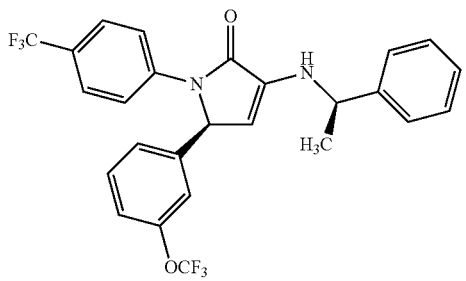

and

Preparation Ib (R)-1-(4-Trifluoromethyl-phenyl)-3-((R)-1-phenyl-ethylamino)-5-[3-trifluoromethoxy-phenyl]-1,5-dihydro-pyrrol-2-one

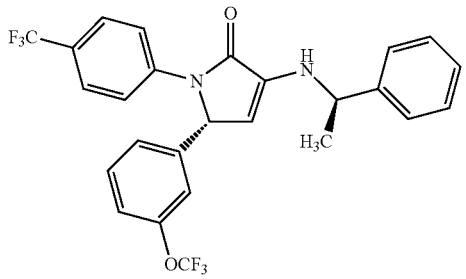

Add (R)-(+)-α-methyl benzylamine (45.0 mL, 349.8 mmol) to the organic layer described in Preparation I containing the (±)-5-(3-trifluoromethoxy-phenyl)-1-(4-trifluoromethyl-phenyl)-pyrrolidine-2,3-dione. Stir the solution at ambient temperature for 72 hours. Concentrate the reaction mixture and purify by silica gel chromatography (5-15%

EtOAc-hexane) to yield (S)-1-(4-trifluoromethyl-phenyl)-3-((R)-1-phenyl-ethylamino)-5-(3-trifluoromethoxy-phenyl)-1,5-dihydro-pyrrol-2-one (32.4 g, 37%) as a tan foam and (R)-1-(4-trifluoromethyl-phenyl)-3-((R)-1-phenyl-ethylamino)-5-(3-trifluoromethoxy-phenyl)-1,5-di hydro-pyrrol-2-one (26.0 g, 29%) as a pale orange oil.

(S)-1-(4-trifluoromethyl-phenyl)-3-((R)-1-phenyl-ethylamino)-5-(3-trifluoromethoxy-phenyl)-1,5-dihydro-pyrrol-2-one $^1$H NMR (400 MHz, DMSO-d$_6$) δ 7.74 (d, 2H, J=8.8 Hz), 7.62 (d, 2H, J=8.8 Hz), 7.39-7.34 (m, 3H), 7.28 (dd, 2H, J=7.7, 7.1 Hz), 7.21-7.14 (m, 4H), 6.04 (d, 1H, J=7.5 Hz), 5.91 (d, 1H, J=2.6 Hz), 5.21 (d, 1H, J=2.6 Hz), 4.31-4.23 (m, 1H), 1.42 (d, 3H, J=7.0 Hz). MS (m/z): 507 (M+1).

(R)-1-(4-trifluoromethyl-phenyl)-3-((R)-1-phenyl-ethylamino)-5-(3-trifluoromethoxy-phenyl)-1,5-dihydro-pyrrol-2-one $^1$H NMR (400 MHz, DMSO-d$_6$) δ 7.76 (d, 2H, J=8.8 Hz), 7.62 (d, 2H, J=8.8 Hz), 7.34 (d, 2H, J=7.0 Hz), 7.28-7.20 (m, 3H), 7.14-7.06 (m, 2H), 7.02 (d, 1H, J=7.9 Hz), 6.96 (s, 1H), 5.96-5.92 (m, 2H), 5.19 (d, 1H, J=2.6 Hz), 4.36-4.27 (m, 1H), 1.44 (d, 3H, J=7.0 Hz). MS (m/z): 507 (M+1).

Example 3

(3R,5R)-3-[1-Methyl-1-(6-trifluoromethyl-pyridin-3-yl)-ethylamino]-1-(4-trifluoromethyl-phenyl)-5-(3-trifluoromethoxy-phenyl)-pyrrolidin-2-one

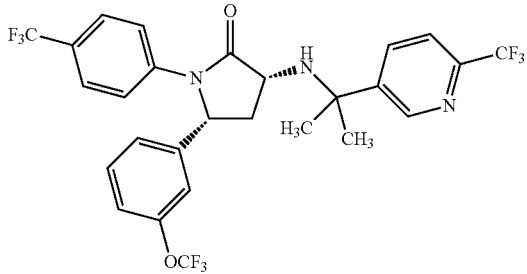

and

Example 4

(3S,5R)-3-[1-Methyl-1-(6-trifluoromethyl-pyridin-3-yl)-ethylamino]-1-(4-trifluoromethyl-phenyl)-5-(3-trifluoromethoxy-phenyl)-pyrrolidin-2-one

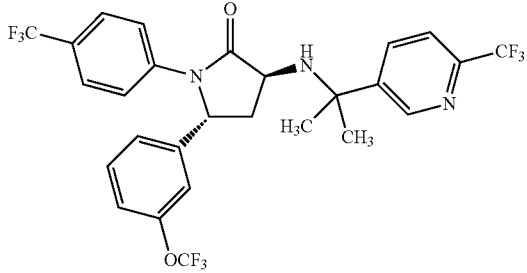

Add trifluoroacetic acid (21.6 mL, 285 mmol) dropwise to a biphasic mixture of (R)-1-(4-trifluoromethyl-phenyl)-3-((R)-1-phenyl-ethylamino)-5-(3-trifluoromethoxy-phenyl)-1,5-dihydro-pyrrol-2-one (28.9 g, 57.1 mmol) in toluene (144 mL) and water (58 mL). Stir at ambient temperature for 60 minutes. Observe significant formation of (R)-5-[3-trifluoromethoxy-phenyl]-1-(4-trifluoromethyl-phenyl)-pyrrolidine-2,3-dione (LC MS 85%, Ret. time=4.27 minutes, Method D) MS (m/z): 402 (M−1).

Separate the aqueous layer and wash the toluene layer with water, pH 7 buffer and saturated sodium chloride solution. Add acetic acid (26.2 mL, 456 mmol) and 1-methyl-1-(6-trifluoromethyl-pyridin-3-yl)-ethylamine (23.3 g, 114 mmol) to the toluene solution containing (R)-5-[3-trifluoromethoxy-phenyl]-1-(4-trifluoromethyl-phenyl)-pyrrolidine-2,3-dione. Heat to 55° C. for 18 hours. Observe significant formation of (R)-3-[1-methyl-1-(6-trifluoromethyl-pyridin-3-yl)-ethylamino]-5-(3-trifluoromethoxy-phenyl)-1-(4-trifluoromethyl-phenyl)-1,5-dihydro-pyrrol-2-one (LC MS 100%, Ret. time=5.59 minutes, Method D, MS (m/z): 590 (M+1). Concentrate under reduced pressure. Dissolve the crude (R)-3-[1-methyl-1-(6-trifluoromethyl-pyridin-3-yl)-ethylamino]-5-(3-trifluoromethoxy-phenyl)-1-(4-trifluoromethyl-phenyl)-1,5-dihydro-pyrrol-2-one in acetic acid (285 mL) and add sodium cyanoborohydride (7.2 g. 114 mmol). Stir 1.75 hours at ambient temperature and concentrate under reduced pressure. Dissolve the residue in ethyl acetate and wash with saturated sodium bicarbonate solution, water and saturated sodium chloride solution. Dry the solution over sodium sulfate, filter and concentrate under reduced pressure. Purify the residue by silica gel chromatography (10-30% ethyl acetate-hexane) to obtain (3R,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one (18.0 g, 53%) as a yellow oil and (3S,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one (0.92 g, 2.7%) as an oil.

(3R,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one $^1$H NMR (400 MHz, DMSO-d$_6$) δ 8.96 (d, 1H, J=2.2 Hz), 8.24 (dd, 1H, J=8.4, 1.8 Hz), 7.80 (d, 1H, J=8.4 Hz), 7.57 (d, 2H, J=8.8 Hz), 7.47 (d, 2H, J=8.4 Hz), 7.36 (dd, 1H, J=7.8, 7.8 Hz), 7.26 (d, 1H, J=7.9 Hz), 7.21 (s, 1H), 7.12 (d, 1H, J=8.1 Hz), 5.25 (dd, 1H, J=9.7, 6.2 Hz), 3.47-3.39 (m, 1H), 2.89 (d, 1H, J=4.4 Hz), 2.70 (dd, 1H, J=13.3, 6.9, 5.2 Hz), 1.65 (dd, 1H, J=21.8, 10.4 Hz), 1.48 (s, 3H), 1.44 (s, 3H).
MS (m/z): 592 (M+1).

Salt formation: tosylate—Add one equivalent p-toluenesulfonic acid monohydrate and crystallize from isopropanol. Yield 85%, MS (m/z): 592 (M+1).

Salt formation: hydrochloride—Add one equivalent of hydrochloric acid in diethyl ether to form the hydrochloride salt and recrystallize from isopropanol. Yield 63%, MS (m/z): 592 (M+1).

(3S,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one $^1$H NMR (400 MHz, DMSO-d$_6$) δ 8.92 (s, 1H), 8.19 (d, 1H, J=7.9 Hz), 7.78-7.70 (m, 3H), 7.64 (d, 2H, J=8.8 Hz), 7.39-7.34 (m, 1H), 7.20-7.12 (m, 2H), 7.10 (s, 2H), 5.62 (d, 1H, J=8.3 Hz), 3.50-3.43 (m, 1H), 2.86 (d, 1H, J=4.0 Hz), 2.43-2.33 (m, 1H), 2.09-2.02 (m, 1H), 1.46 (s, 3H), 1.43 (s, 3H),
MS (m/z): 592 (M+1).

Salt formation: tosylate—Add one equivalent p-toluenesulfonic acid monohydrate and crystallize from isopropanol-heptane. Yield 80%, MS (m/z): 592 (M+1).

CB$_1$ and CB$_2$ In Vitro Functional Assays

Antibody-Capture SPA GTP-γ-$^{35}$S Binding

In cell membranes expressing human or rat CB$_1$ or CB$_2$ receptor, test (3R,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one 4-methylbenzenesulfonate (referred to as "Example 2") for its antagonist/inverse agonist functional GTP-binding. In a 96 well format using a modified antibody capture technique (DeLapp et al., 1999), measure GTP-γ$^{35}$S binding. Briefly incubate for 30 minutes at room temperature the GTP-binding assay buffer (20 mM Hepes, 100 mM NaCl, 5 mM MgCl$_2$, pH 7.4), the CHO or Sf9 cell membranes expressing CB$_1$ or CB$_2$, (Applied Cell Sciences, Gaithersburg, Md.; PerkinElmer Life Sciences, Boston, Mass.; prepare membranes as previously described (DeLapp et al., 1999)), Example 2 and the 500 pM GTP-γ-$^{35}$S (PerkinElmer Life Sciences, Boston, Mass.). Perform antagonist dose responses in the presence of a saturating dose of a full agonist (methanandamide). To the 96 well plate, in addition, add a mixture containing 0.27% Nonidet P40 detergent (Roche, Indianapolis, Ind.), anti-Gi antibody (final dilution of 1:300; Covance, Princeton, N.J.), and 1.25 mg anti-rabbit antibody scintillation proximity assay beads (GE Healthcare, Piscataway, N.J.) and seal the plates and incubate for an additional 3 hours. Centrifuge the plates at 700×g for 10 minutes using a Beckman GS-6R centrifuge and count for 1 minute per well using a Wallac MicroBeta TriLux scintillation counter (PerkinElmer, Boston, Mass.).

To analyze data, subtract background from all wells. Determine percent agonist efficacy by normalizing agonist/inverse agonist dose response data to a full agonist (methanandamide) response. Calculate antagonist percent inhibition data by normalizing to results generated with a saturating concentration of agonist (methanandamide). Analyze the data using a 4-parameter logistic reduced fit with Activity Base and XLFit3 (IDBS, Emeryville, Calif.). Determine K$_b$ values using a modification of the Cheng-Prusoff relationship: K$_b$=IC50/(1+[agonist]/EC50) where IC50 is determined from a four parameter fit of displacement curves, [agonist]=EC50 of full agonist, and EC50 is determined from a four parameter fit of a full agonist concentration response curve (Cheng and Prusoff 1973). Calculate mean K$_b$ values as a mean of at least three independent determinations±standard error of the mean (SEM).

Table 1 summarizes the antagonist/inverse agonist properties of Example 2 in CHO cells expressing human or rat CB$_1$ receptors or Sf9 cells expressing human CB$_2$ receptors. It is concluded Example 2 exhibits potent human and rat CB$_1$ antagonism with no measurable antagonism of the human CB$_2$ receptor. The data indicates Example 2 is a potent CB$_1$ antagonist/inverse agonist at both rat and human receptors with no antagonism of human CB$_2$ receptors.

Table 2 summarizes the agonist properties of Example 2 in Sf9 cell membranes from cells expressing human CB$_1$ or CB$_2$ receptors. These data demonstrate that Example 2 is an inverse agonist at the human CB$_1$ receptor as evidenced by agonist efficacy (Table 2) less than zero which indicates that the compound decreased basal constitutive activity of the CB$_1$ receptor in vitro. Example 2 does not have any measurable CB$_2$ agonist activity (Table 2).

REFERENCES

DeLapp N W, McKinzie J H, Sawyer B D, Vandergriff A, Falcone J, McClure D and Felder C C (1999). Determination of [$^{35}$S]guanosine-5'-O-(3-thio)triphosphate binding mediated by cholinergic muscarinic receptors in membranes from Chinese hamster ovary cells and rat striatum using an anti-G protein scintillation proximity assay. *J Pharmacol Exp Ther* 289:946-955.

Cheng Y C and Prusoff W H. 1973. Relationship between the inhibition constant (Ki) and the concentration of inhibitor which causes 50 percent inhibition (150) of an enzymatic reaction. Biochem Pharmacol 22:3099-3108.

TABLE 1

In Vitro CB$_1$ and CB$_2$ Antagonist/Inverse Agonist Functional
GTP-Binding for Example 2 in CHO or Sf9 Cell Membranes
Expressing Human or Rat CB1 or CB2 Receptor

| GTP Binding Assay (CHO or Sf9 cell membranes) | Inverse Agonist Potency (K$_b$, nM) |
|---|---|
| Human CB$_1$ (CHO cells) | 0.71 ± 0.26 |
| Rat CB$_1$ (CHO cells) | 1.27 ± 0.20 |
| Human CB$_2$ (Sf9 cells) | No measurable activity |

TABLE 2

In vitro CB$_1$ and CB$_2$ Agonist GTP-Binding for Compound 2 in
Cell Membranes from Sf9 Cells Expressing Human Receptors

| GTP Binding Assay (Sf9 membranes) | Agonist Potency EC50 (nM) | Agonist Efficacy % |
|---|---|---|
| Human CB$_1$ | 0.58 ± 0.05 | −47.9 ± 4.7 |
| Human CB$_2$ | No measurable activity | 0 |

Forced Swim Test (FST)

Receive NIH male Swiss mice (Harlan Sprague-Dawley, weight 20-25 g) 7 to 10 days prior to testing. House 12 mice per cage. Test only animals that weigh 25-30 g. On the day of testing, bring animals to the testing room at least 1 hour prior to dosing. When dosing starts, dose at 6-8 minute intervals between each dose with each mouse receiving either Administer vehicle (1% CMC, 0.5% SLS, 0.08% povidone, 0.05% antifoam) or Example 2, p.o. Next, place mice in a clean cage (4 mice per cage). After 90 minutes, start the test following a 90 minute pre-treatment with Example 2 or vehicle.

Mice FST: Place NIH-Swiss mice in clear plastic cylinders (diameter: 10 cm; height: 25 cm) filled to 6 cm with 22-25° C. water for six minutes. Record the duration of immobility during the last 4 minutes of the six-minute trial. A mouse is regarded as immobile when floating motionless or making only those movements necessary to keep its head above the water. Analyze data by ANOVA with a post-hoc Dunnett's test (alpha=0.05; JMP). Record the minimum effective dose (MED) as the lowest dose of compound at which statistically significant decrease in immobility time is observed versus a vehicle control.

Bioavailability

Methods for accessing bioavailability are well appreciated in the art. One such reference is *Medicinal Research Reviews* Vol. 21 No. 5 382-396 (2001).

TABLE 3

Antagonist/inverse agonist, selectivity, (FST) and bioavailability properties of various salts of (3R,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one.

| Exemplified Compound | Antibody-Capture SPA GTP-γ-$^{35}$S Binding Inverse Agonist Potency | | Bio-availability Rat | Bio-availability Dog | FST (MED mg/kg p.o.) |
| --- | --- | --- | --- | --- | --- |
| | CB$_1$ (K$_b$, nM)* | CB$_2$ (K$_b$, nM) | | | |
| Example 2 | 2.7** | No measurable activity | 65% | 60% | 1 |
| Example 3 (HCl salt) | 0.70 | No measurable activity | ND | ND | ND |
| Example 4 (Tosylate salt) | 3.0 | No measurable activity | ND | ND | ND |

TABLE 3-continued

Antagonist/inverse agonist, selectivity, (FST) and bioavailability properties of various salts of (3R,5R)-3-[1-methyl-1-(6-trifluoromethyl-pyridin-3-yl)-ethylamino]-1-(4-trifluoromethyl-phenyl)-5-(3-trifluoromethoxy-phenyl)-pyrrolidin-2-one.

| Exemplified Compound | Antibody-Capture SPA GTP-$\gamma$-$^{35}$S Binding Inverse Agonist Potency | | Bio-availability Rat | Bio-availability Dog | FST (MED mg/kg p.o.) |
|---|---|---|---|---|---|
| | $CB_1$ ($K_b$, nM)* | $CB_2$ ($K_b$, nM) | | | |
| 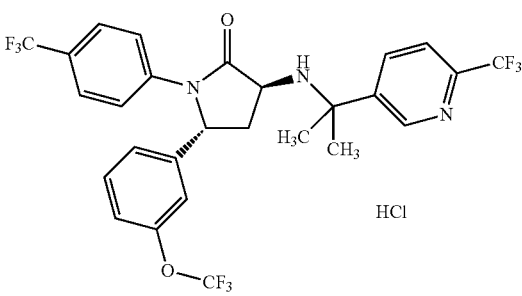 Example 4 (HCl salt) | 8.8 | No measurable activity | ND | ND | ND |

*hCB$_1$ SPA GTP$\gamma^{35}$S Sf9 Mem 22.7 ug protein/well Antagonist
**1-test Sf9 Table 3 vs. CHO Table 1, p = 0.127/ND = not determined

Cortical Activation cFos Activation

Characterize Example 2 for its ability to activate gene expression and neurochemical efflux in cortical and subcortical regions and to interact with the prototypical atypical antipsychotic agent clozapine.

Methods: House Male Sprague Dawley rats (155-175 g) for 1 week prior to experimentation. Prepare Example 2 in a vehicle suspension of 1% Sodium carboxymethyl cellulose, 0.5% Sodium lauryl sulfate, 0.05% Antifoam, 0.085% Povidone and administer, to rats (e.g., male Sprague Dawley rats, 155-175 g) p.o. (a dose of 1 or 10 mg/kg). Control rats receive vehicle. Administer clozapine (Sigma) 1 hour later at a concentration of 8 mg/mL in a vehicle solution of 0.4% lactic acid at a dose of 8 mg/kg s.c. Sacrifice animals (n=7-8 per group) by decapitation 2 hours after administration of clozapine or vehicle for clozapine. Remove rapidly whole brains and immediately immerse in isopentane (2-methyl butane) over dry ice. Cut coronal sections through the prefrontal cortex (PFC), nucleus accumbens (NAc) and dorsolateral striatum (DL-Str) at 14 µm and perform Fos immunohistochemistry. Assess atypicality index (Robertson et al., 1994) using the following formula: Atypical Index=(NAcD−NAcV)−(DL-StrD−DL-StrV) where the average number of Fos-li neurons in NAc=nucleus accumbens, D=drug, V=vehicle, DL-Str=dorsolateral striatum. Analyze data using a one-way ANOVA followed by Newman-Keul's post hoc test (Graph Pad Prism 4.03). Set the level of significance at P<0.05.

Results: Clozapine and Example 2 both individually tend to or significantly enhance cortical and subcortical Fos reactivity. Observe Example 2 enhancing the effects of clozapine alone at both 1 and 10 mg/kg, p.o.

Conclusions: Increase cFos expression in rat brain in both prefrontal cortex and subcortical regions by Example 2. Display a similar spectrum of neural activation by clozapine. Addition of Example 2 to clozapine results in augmentation of cFos expression induced by clozapine in brain areas critical to cognitive function and negative symptom control. Observe the overall effect of Example 2 to the clozapine effect producing a neural signature of greater atypicality with respect to ventral vs. dorsal striatal impact.

Stimulation of Monoamine Neurotransmitter Release and Turnover in Brain Regions Associated with Cognition Methods: Implant male Sprague-Dawley rats (260-300 g, Taconic Farms, Germantown, N.Y.) with a cannula (BAS, West Lafayette, Ind.) in the prefrontal cortex (PFC) 5-7 days before the experiment. Insert a concentric type probe with a 4 mm membrane tip extending below the cannula through the cannula about 16 hours before the experiment began and collect the microdialysate from prefrontal cortex and analyze for monoamines and their metabolites. Calculate all microdialysis data as percent change from dialysate basal concentrations with 100% defined as the average of the final three drug pre-injection values and each group having 5-6 rats. Analyze data with ANOVA and follow by a post-hoc Bonferroni test. Results: Increase rat cortical monoamine and metabolite levels by Example 2 doses as low as 1 mg/kg, p.o.

Ethanol Seeking Behaviors: 12-Hour Ethanol Consumption in Alcohol-Preferring Rats (P Rats)

Evaluate Example 2 for its ability to reduce consumption of ethanol in rats selectively bred for high oral ethanol intake (P rats). In addition, study the effects of Example 2 under conditions in which effects of the compound on motivation or the control of behavior by ethanol could be assessed.

Methods: Study the effects of Example 2 on female, alcohol-preferring (P) rats on alcohol consumption under a continuous free access paradigm. For comparative purposes test the standard opioid antagonist naltrexone. Monitor voluntary consumption of 15% (v/v) ethanol. Suspend Example 2 in vehicle (1% CMC, 0.5% SLS, 0.08% povidone, 0.05% Dow Corning antifoam 1510 US) and give p.o. 3 hours prior to the onset of the dark cycle. In addition, measure locomotor activity via infrared sensor.

Results: Consumption of ethanol but not water was decreased in a dose-dependent manner by orally-administered Example 2. Naltrexone, at higher doses, was also able to reduce ethanol intake. Example 2 did not significantly alter locomotor activity of these rats until a dose of 10 mg/kg.

Ethanol Seeking Behaviors: Progressive Ratio Responding Maintained by Ethanol

Assess the ability of Example 2 to reduce the motivational drive controlling ethanol intake.

Methods: Study female alcohol-preferring (P) rats under a progressive ratio schedule in which responding produces 15% ethanol (v/v). Under the progressive ratio schedule, the response requirement for ethanol delivery increases from 1 to 2 and then increments by 2 after 3 ethanol presentations.

Results: Reduce ethanol-seeking behavior and the consumption of ethanol consumed by administration of Example 2 dose-dependently. Reduce Example 2 the breakpoint (the amount of work the rat would accomplish for a fixed quantity of ethanol) in a dose-dependent manner [$F(4,20)=4.52$, $p=0.009$].

In Vivo Efficacy in Feeding Models

Methods: Administer Example 2 to diet-induced obese (DIO) male Long-Evans rats. Establish DIO by ad lib feeding from weanling of a diet consisting of 40% fat, 39% carbohydrate and 21% protein caloric content for at least 12 weeks. Define compound potency by T17 (the dose required to produce a difference from the vehicle group of 17 grams). This represents a minimally biologically relevant reduction of 3-4% of body weight compared to vehicle treatment after 2 weeks.

Results: Decrease cumulative food intake by administrating Example 2 once daily orally throughout the 14-day study. Consistent with reduced food intake, observe reduction of cumulative body weight following the 14-day oral treatment with Example 2, producing an estimated T17 of 0.13 mg/kg. Measure body composition analysis by quantitative nuclear magnetic resonance (QNMR) showing significant reductions in fat mass at doses ranging from 0.1-10 mg/kg with minimal changes in fat free mass at one of the highest doses.

Atypical Antipsychotic Weight Gain Model

Methods: Maintain adult lean, female Sprague-Dawley rats ad libitum on normal rodent chow Purina LabDiet 5001 (12.3% fat) and water. Treat one group (n=7) with vehicle (1% lactic acid) on days 1-14 vehicle while treating the rest with olanzapine (2 mg/kg, po). Follow food intake, monitor body weight and change in fat mass over a two week treatment. After 14 days of drug delivery, divide the olanzapine treated animals (n=8 per group) and treat one group with 0.3 mg/kg Example 2 plus olanzapine, treat a second group with 1 mg/kg Example 2 plus olanzapine and treat the final group with vehicle plus olanzapine for days 15-28.

Results: Observe treatment emergent increases in cumulative food intake, body weight and fat mass compared to vehicle treated controls with once daily oral administration for 14-days of olanzapine. Addition of Example 2 and the olanzapine treatment results in a significant reduction in fat mass gain with both doses of Example 2 with no changes in fat free mass.

Conclusions: Produce a significant reduction in body weight from vehicle treated controls by daily oral administration of Example 2 for 14 days to diet-induced obese (DIO), male Long-Evans rats maintained on a high-energy diet reduced food intake. Estimate the efficacy dose (T17) of 0.13 mg/kg/day for Example 2 for producing a change in body mass from control. Analyze changes in body composition to determine that the reduced body mass results from a significant reduction in fat mass at doses up to 10 mg/kg (the highest dose tested). Evaluate with a once daily oral administration of Example 2 for 14 days to two week olanzapine treated, female Sprague-Dawley rats to help to produce a significant reduction in fat mass compared to that of olanzapine treated controls.

I claim:

1. A compound of Formula

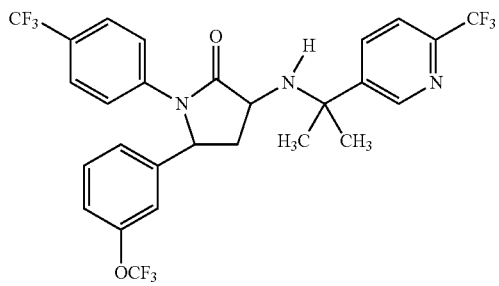

or a pharmaceutically acceptable salt thereof.

2. The compound of claim 1, having Formula

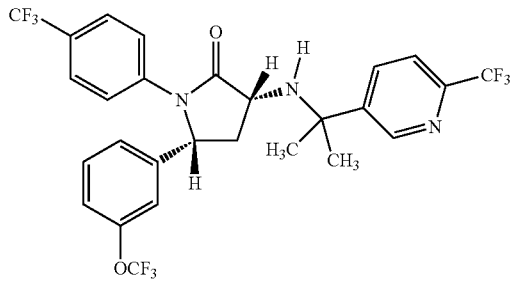

or a pharmaceutically acceptable salt thereof.

3. A pharmaceutical composition comprising a compound according to claim 1 and a pharmaceutically acceptable carrier, diluent, or excipient.

4. The pharmaceutical composition of claim 3, wherein the compound of the Formula

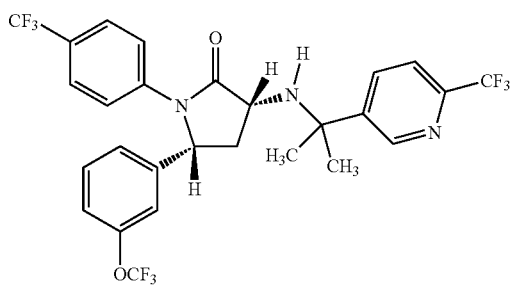 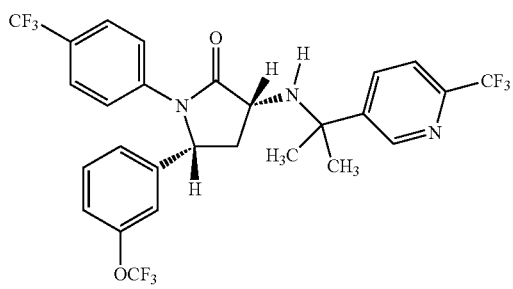
is present in optical purity greater than 90% ee.
5. The pharmaceutical composition of claim 3, wherein the compound of the Formula
is present in optical purity greater than 95% ee.
* * * * *